US012257175B2

(12) United States Patent
Shaviv et al.

(10) Patent No.: US 12,257,175 B2
(45) Date of Patent: Mar. 25, 2025

(54) INTRAVAGINAL DEVICE

(71) Applicant: Gals Bio Ltd., Mevaseret Zion (IL)

(72) Inventors: Hilla Shaviv, Mevaseret Zion (IL); Nadav Cohen, Haifa (IL); Omer Shezifi, Haifa (IL); Daniel Rosenblum, Ramat Hasharon (IL)

(73) Assignee: Gals Bio Ltd., Mevaseret Zion (IL)

( * ) Notice: Subject to any disclaimer, the term of this patent is extended or adjusted under 35 U.S.C. 154(b) by 1057 days.

(21) Appl. No.: 17/050,447

(22) PCT Filed: May 3, 2019

(86) PCT No.: PCT/IB2019/053623
§ 371 (c)(1),
(2) Date: Oct. 25, 2020

(87) PCT Pub. No.: WO2019/211802
PCT Pub. Date: Nov. 7, 2019

(65) Prior Publication Data
US 2021/0137725 A1    May 13, 2021

Related U.S. Application Data

(60) Provisional application No. 62/666,157, filed on May 3, 2018.

(51) Int. Cl.
*A61B 5/00* (2006.01)
*A61F 5/455* (2006.01)
(Continued)

(52) U.S. Cl.
CPC ......... *A61F 5/4553* (2013.01); *A61B 5/4337* (2013.01); *A61M 31/002* (2013.01); *A61F 13/2045* (2013.01); *A61M 2210/1475* (2013.01)

(58) Field of Classification Search
CPC ...... A61F 5/4553; A61F 13/2045; A61F 6/08; A61F 2/005; A61M 2210/1475;
(Continued)

(56) References Cited

U.S. PATENT DOCUMENTS 5,483,976 A * 1/1996 McLaughlin ......... A61M 31/00
128/885
6,332,878 B1 * 12/2001 Wray .................... A61F 5/4556
128/830

(Continued)

FOREIGN PATENT DOCUMENTS

WO    2017/015767    2/2017

OTHER PUBLICATIONS

PCT Search Report and Written Opinion PCT/IB2019/053623, Aug. 29, 2019.

*Primary Examiner* — Shefali D Patel
*Assistant Examiner* — William R Frehe
(74) *Attorney, Agent, or Firm* — Dekel Patent Ltd.; David Klein

(57) ABSTRACT

An intravaginal device (1600) includes arms (1602) and struts (1604). Each strut of the struts (1604) has a first end (1610) coupled to a shaft (1606) arranged to slide in a tube (1608) and a second end (1612) coupled to one of the arms (1602). A string (1616) is coupled to the shaft (1606). The arms (1602) have a stowed orientation in which the struts (1604) are folded inwards and a deployed orientation in which the struts (1604) point radially outwards and tautly hold the arms (1602) in an expanded position.

8 Claims, 7 Drawing Sheets

(51) Int. Cl.
*A61M 31/00* (2006.01)
*A61F 13/20* (2006.01)

(58) Field of Classification Search
CPC ..... A61K 9/0034; A61K 9/0036; A61P 15/02; A61B 5/150045
See application file for complete search history.

(56) References Cited

U.S. PATENT DOCUMENTS

| | | | |
|---|---|---|---|
| 2008/0281149 A1 | 11/2008 | Sinai | |
| 2009/0318750 A1* | 12/2009 | Ziv | A61F 2/005 600/29 |
| 2011/0087155 A1* | 4/2011 | Uhland | A61N 1/327 604/501 |
| 2016/0220342 A1 | 8/2016 | Ziv | |

* cited by examiner

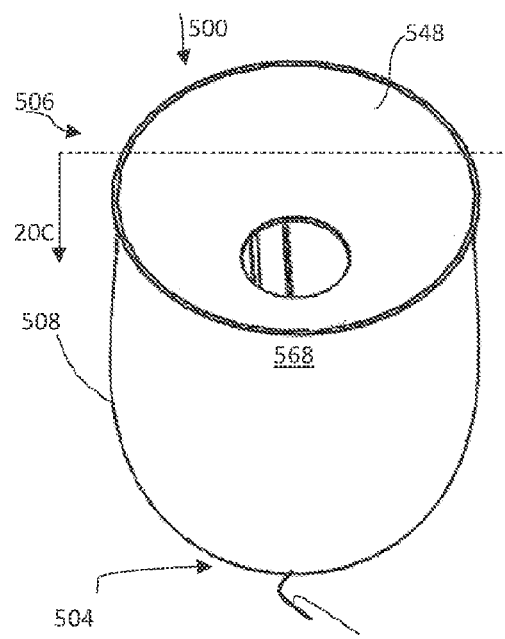
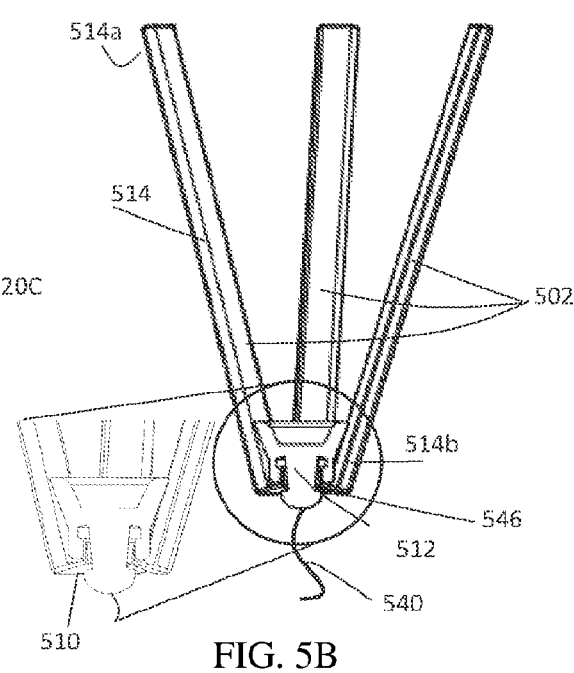
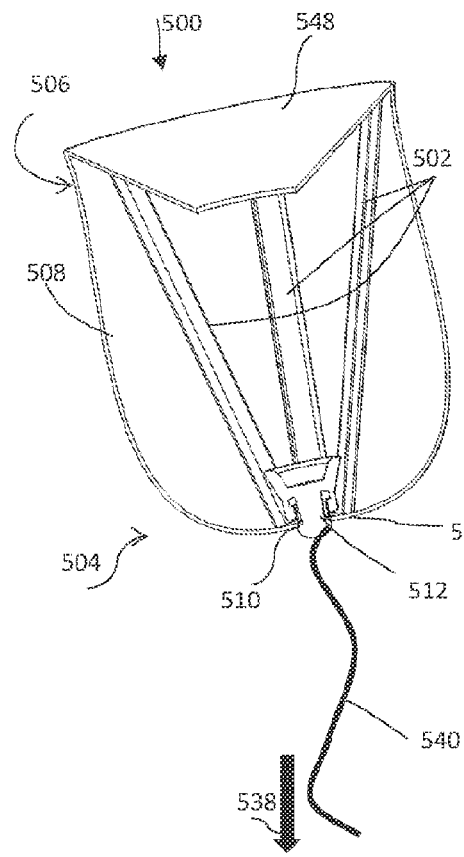
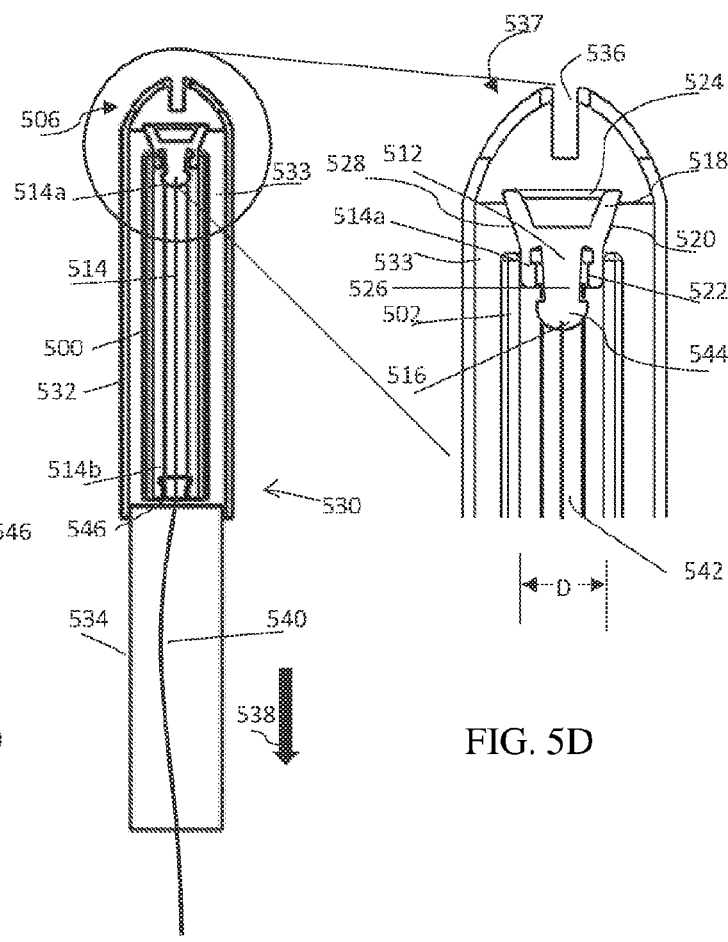
FIG. 5A
FIG. 5B
FIG. 5C
FIG. 5D

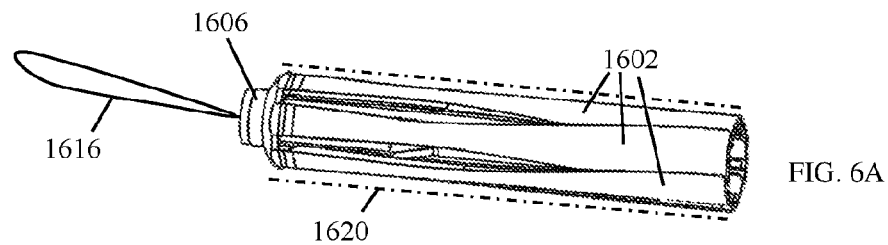
FIG. 6A
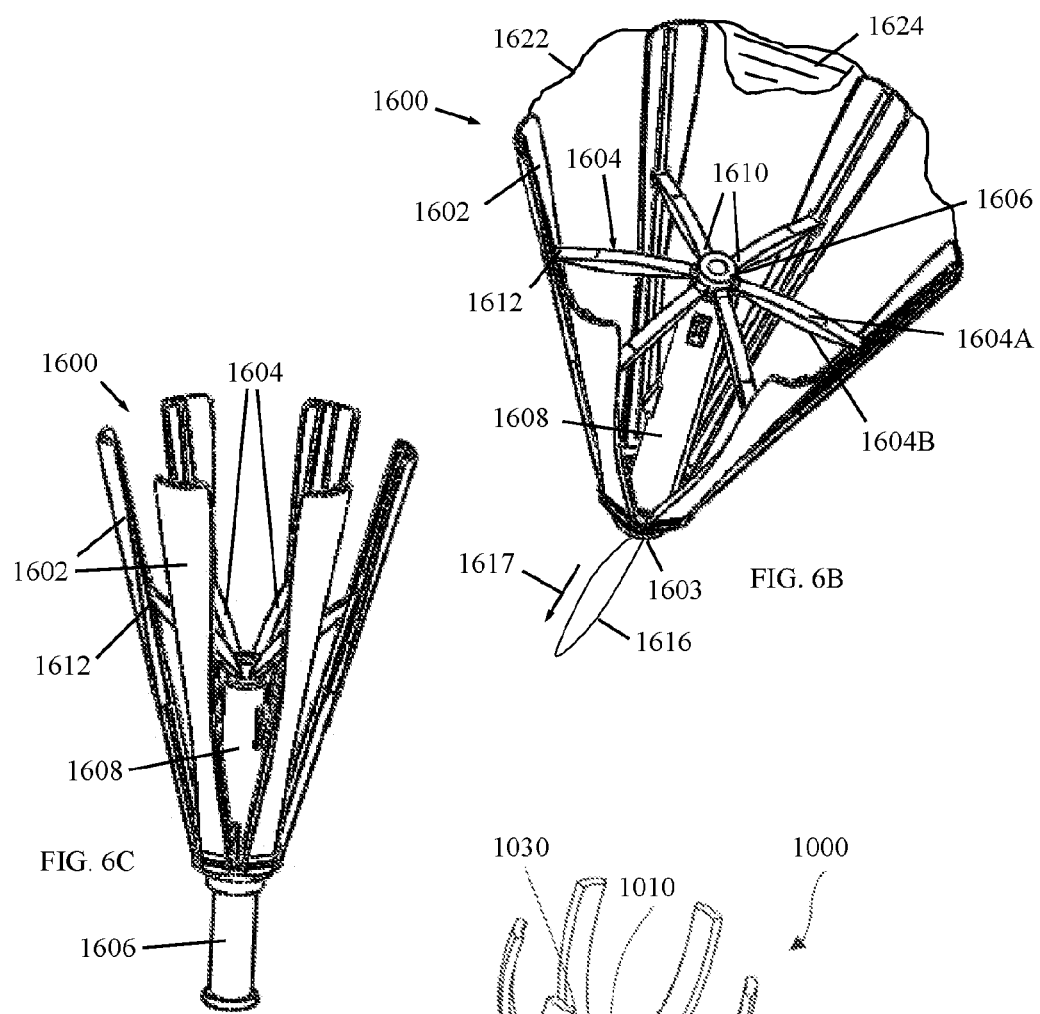
FIG. 6B
FIG. 6C
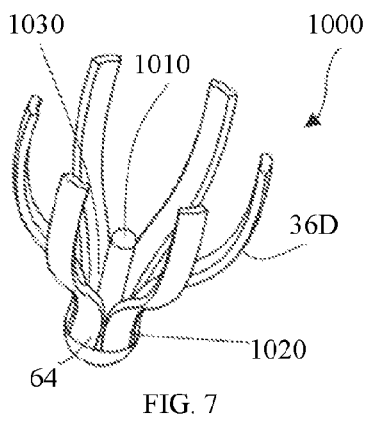
FIG. 7

INTRAVAGINAL DEVICE

FIELD OF THE INVENTION

The present invention, in some embodiments thereof, relates to a gynecological device and, more particularly, but not exclusively, to a collapsible and expandable intravaginal device suitable for at least one gynecological purpose in particular and women's health in general.

BACKGROUND OF THE INVENTION

Many gynecological devices are known in the art for various uses such as, for example, contraception, the blocking or collection of menses of the human female, and the release of pharmacological substances into the vaginal cavity. These include high absorbency tampons wherein menses fluid is absorbed into the material of the tampons, cups that block the passage of vaginal secretions and/or menses fluid discharged from the cervix, vaginal carriers which release pharmaceutical substances, and other intravaginal devices having various materials, structures and purposes.

U.S. Pat. No. 5,295,984 (Contente et al.) is an example of a vaginal discharge collection device, which has an elastomeric rim and a flexible film reservoir.

U.S. Pat. No. 6,168,609 (Kamen et al.) discusses a catamenial collector that "has a receptacle with a flexible hollow rim capable of inflation and has a handle with substantially the length of a female vagina. The collector may have a string . . . extending through the rim and at least a portion of the handle so that a pulling force axially applied to a string end causes the receptacle to close. In another embodiment, an elastic member is so configured that deflation of the rim also causes the receptacle to close" (abstract).

U.S. Pat. No. 9,827,136 to Applicant discusses a "catamenial device . . . including: a flexible resilient menstrual cup (MC), which includes: at least two resilient ribs extending inwardly from the inner surface of the MC base; an elastic rim frame connected to the top of the ribs; a reservoir bag connected to the rim in a sealed manner for collecting the menstrual fluid; and a withdrawal string . . . The MC has a drogue like structure comprising at least two flexible ribs having arcuate vertical struts (AVS) structure connected to a flat base. The ribs are connected to the elastic rim frame with at least two flexible arcuate horizontal struts (AHS)" (abstract).

U.S. Pat. No. 6,332,878 (Wray et al.) discusses a device which "has a cup shaped to fit over the cervix and has an attached pouch defining a reservoir that contains an absorbent material. A port having a fabric cover permits menstrual flow from the uterus to pass into the reservoir. The device, which is flexible and resilient, is folded in one end of an applicator used to insert the device into the vagina. The device is shaped to automatically fit into and remain in position over the cervix after the device is ejected from the applicator" (abstract).

U.S. Pat. No. 4,381,771 teaches a "contraceptive, cervical cover, including a dome-like main portion which is shaped to cover the cervix, long extending lips which form a one-way valve to permit waste material to out of the cervix and an outwardly biased collar which holds the cover securely to the walls of the vaginal surrounding the cervix."

Additional background art includes U.S. Pat. No. 7,771,344 (ConTIPI Ltd.); WO 2017/010800 (Loon Lab); and WO 2016 042310 (Goodwin, et al.), KR 20160109503A, and U.S. Patent Application Publication No. 2016/0278988.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5A is a perspective view of a device in accordance with a further embodiment of the invention, the device including an optional one-way valve;

FIG. 5B is a cross-sectional view of components of the device shown in FIG. 5A, the membrane and optional valve components of the device having been omitted for clarity, wherein a portion of the device is enlarged for clarity;

FIG. 5C is a cross-sectional view of the device shown in FIG. 5A, taken in the direction of arrows C-C therein, according to some embodiments of the invention;

FIG. 5D is a cross-sectional view of components of the device shown in FIG. 5A, the device contained in an applicator, according to some embodiments of the present invention, wherein the membrane and optional valve components of the device have been omitted and a portion of the components and applicator has been enlarged for clarity;

FIGS. 6A-6C are simplified pictorial illustrations of an intravaginal device, in accordance with a non-limiting embodiment of the invention, respectively with the device in an applicator, after deployment from the applicator and after collapsing the device for withdrawal from the vagina; and FIG. 7 is a perspective view of a device according to some embodiments of the invention.

DETAILED DESCRIPTION

Figure 1A:
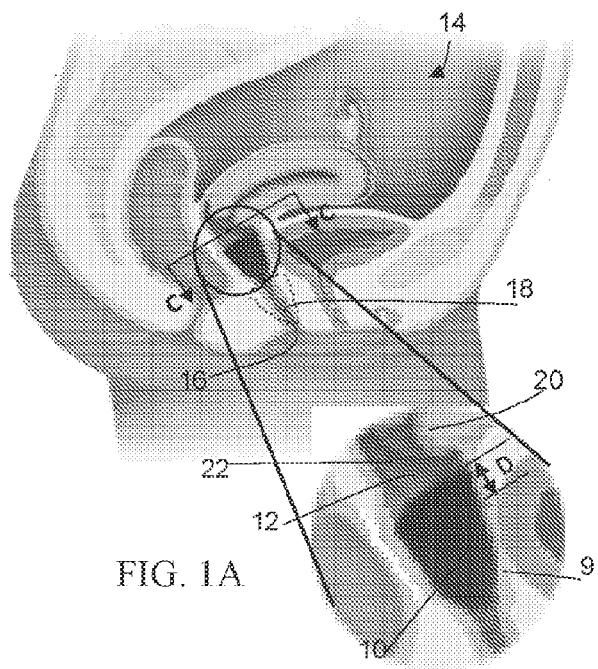
FIG. 1A is a side view of an intravaginal device according to some embodiments of the present invention, in an exemplary position within a vaginal cavity of a human female, wherein a portion of the human female and the device positioned therein is shown in an enlarged view, and wherein the device is shown in dotted lines in an alternate exemplary position within the vaginal cavity.

The present invention, in embodiments, relates to a gynecological device and, more particularly, but not exclusively, to an expandable intravaginal device suitable for at least one gynecological or female quality of life purpose. These include the collection of discharge of the female human such as, for example, during menstruation; the release of a substance or substances in a vaginal cavity of the human female; monitoring pH level of the human female; and monitoring body temperature of the human female. Other possible uses are, for example, blood oximetry, measurement of fetal heart rate, and monitoring of fetal body movements, female heart rate, biomarker analysis of vaginal discharge, biomarker analysis of menstrual blood like vitamins, hemoglobin, fertility hormones and more.

The present invention, in some embodiments, includes a cup-shaped structure having a plurality of axially extending elements. In some embodiments, the cup-shaped structure is not rotationally symmetric. In embodiments, there is no rigid rim defined by a single element at the open end of the structure. In embodiments, the axially extending elements and other elements of the device do not define a rigid rim at the open end of the cup-shaped structure to exert a radial force against the vaginal wall. A potential advantage of having no rigid rim at the device open end is facilitating collapsing and of the device and storage of the device in collapsed form for insertion into a vaginal cavity, as discussed herein.

Optionally, the device may be cup-shaped and the body of the device may also be, for example, cone-shaped, truncated-cone shaped, polyhedron-shaped, or cylindrical.

In embodiments, the cup-shaped structure has a lip beginning at its open distal end and, in some embodiments, axially extending elements or other component(s) of the device may be elastically predisposed or otherwise predisposed to expand radially outward against a vaginal wall of a human female. In embodiments, the predisposition of the axially extending elements or other component(s) to expand may provide an outward radial force against the vaginal wall that may provide thereby an optional seal between the device lip and the vaginal wall the seal sufficient to prevent fluid flow past said device when positioned in a vaginal passageway. As discussed herein, it should be noted that, according to some embodiments, sealing of the device against the vaginal wall is optional, for example, in the collection of menses discharge, as collection of a majority of the discharge may be sufficient, in some scenarios or no sealing is needed at all in other scenarios.

The outward radial force of the axially extending elements or other component(s) is sufficient, in some embodiments, to cause the vaginal wall to stretch and to force the device lip into sealing engagement with the vaginal wall, the sealing engagement applied over an axial distance of the device of from 0.1 mm to 2 cm. As noted herein, sealing of the device against the vaginal wall may be optional, in some scenarios.

An aspect of some embodiments of the invention relates to providing a structure wherein the axially extending elements have no rigid rim, the axially extending elements not rigidly connected at their distal ends. Such a rigid connection is not necessary for applying an outward radial force. However, a membrane, as discussed herein, is strong enough to resist the radially outward expansion of the axially extending elements, the device having an outer diameter wide enough to seal the device against the vaginal passageway, in some embodiments, as discussed herein.

The absence of a continuous rigid rim, at the distal end of the device, according to some embodiments, is potentially advantageous, for example, as the device may be easier to insert into the vaginal cavity than a device having a continuous rigid rim. Also, in embodiments, the absence of a rigid rim may have the potential advantages of allowing the axial elements to move circumferentially without interference; facilitating local compression/deformation/twisting of at least one of the axial elements; and allowing the device to be radially compressible and/or foldable/distortable, which may facilitate insertion of the device into a suitable applicator and its storage therein and deployment of the device to a suitable position within the vaginal cavity.

According to some embodiments, the device is provided with an applicator which may facilitate deployment and the opening of the device within the vaginal cavity. The device, when radially compressed or folded/distorted may be housed within the applicator, in some embodiments. The device, in some embodiments, may not expand from its radially compressed or folded/distorted configuration until at least most of the device is outside the applicator According to some embodiments, the device additionally includes a fluid flow retarding membrane attached to upper and/or inner and/or outer surfaces of the axially extending elements, the membrane optionally configured to seal the device against the vaginal wall, the lip defined at least partially by the membrane. Optionally, the membrane is waterproof. The axially extending elements may prevent radial collapse of the membrane, in embodiments, such that it is retained in an open, cup-shaped configuration. In some embodiments, such axially extending elements apply an outward radial force to the inner and/or outer surface of the membrane to retain the membrane in its open configuration and to optionally seal the membrane against the vaginal wall, the force strong enough to stretch the vaginal wall. The outward radial force is in the range of from 0.1-2 Kg (1-20 N), for example, 3N, 5N, 10N, and 15N. In embodiments, a stronger outward radial force has a potential advantage of providing a better seal against a vaginal wall. In embodiments, a weaker outward radial force has a potential advantage of providing a more comfortable deployment and fit of the device in the vaginal cavity.

In embodiments, a rim is formed at the device distal end. In some embodiments, a rim is formed at the device distal end by at least a membrane which is stretched by the axially extending elements. In some embodiments, a rim is formed at the device distal end by at least a membrane which is held taut by the axially extending elements.

In accordance with some embodiments, the membrane and axially extending elements are molded as one piece. Alternatively, in some embodiments, the membrane and axially extending elements are formed as separate components. Optionally, the membrane and/or the axially extending elements are fabricated by, for example, an extrusion process, dipping, injection molding, double injection molding, overmolding, dip molding, CNC (computer numerical control) machining, vacuum forming, and 3-D printing.

In embodiments, a membrane may optionally be provided both interior and exterior to the axially extending elements. Optionally, a membrane having both interior and exterior portions may be fabricated of a single piece of material or may be fabricated of two separate materials such as, for example, by separate injection molding procedures. Optionally, a portion of the membrane provided on the inside of the axially extending elements may be thicker than a portion of the membrane provided on the outside of the axially extending elements, or vice-versa. Optionally, a portion of the membrane provided on the inside of the axially extending elements may function as a one-way valve, retaining collected material inside the device.

In embodiments, the device is grippable at its proximal end, for facilitating device removal from the vaginal cavity. Alternatively, the device according to any of the embodiments discussed herein may be provided with a removal element, e.g., at the device proximal end, for facilitating removal of the device.

In some embodiments, the axially extending elements are interwoven or intersecting. Optionally, the device may have a first, unexpanded cup-shaped configuration having a first length; and a second, expanded cup-shaped configuration having a second length which is less than the first length. In embodiments, the device may also be provided with a locking mechanism to retain the axially extending elements in the second configuration. In embodiments, the axially extending elements are no further apart from each other than approximately 1-2 mm. In embodiments, the device also includes a membrane attached to the axially extending elements, the membrane optionally configured to seal the device against the vaginal wall.

In some embodiments, the device includes a membrane and a plurality of linear axially extending ribs which are hingedly connected. In embodiments, an element is actuated to apply a force on the axially extending ribs, thereby causing them to move radially outwardly at the device distal end whereby, optionally, at least the device distal end achieves a seal against a wall of the vaginal cavity.

In some embodiments, the device includes a spring or a spring-like element including a plurality of axial elements, the device convertible from a radially compressed configuration to an expanded configuration. The device also includes a membrane such that, in the expanded configuration, in some embodiments, the membrane is stretched by the spring or spring-like element.

In some embodiments, the device is provided with a payload component which does not interfere with collapsing/deforming/folding, deployment, functioning, and removal of the device. In embodiments, the payload component may perform at least one or more function, for example, the release of a substance into a vaginal cavity of the human female, monitoring pH level of the human female, monitoring body temperature of the human female, oximetry monitoring, measurement of fetal heart rate, and monitoring of fetal body movements, as discussed further herein.

In some embodiments the device is made in such a way that it can be flushed, i.e., it can be disposed of after usage and its design and materials will comply with safe-to-flush regulations.

In some embodiments the device is completely or partially made from materials that are from biological or renewable sources or which are completely or partially biodegradable.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1A illustrates an expandable intravaginal device 10 according to an embodiment of the present invention, as discussed further herein, the device in an exemplary position within a vaginal cavity 12 of a human female 14. It may be noted that a proximal end 18 of the cavity 12 terminates at a vaginal orifice 16 and that a cervix 20 is located adjacent at a distal end 22 of the cavity 12.

While device 10 is shown in one exemplary position nearer to the distal end of cavity 12, it should be understood that, in embodiments, the device may, optionally, be positioned at any location along the vaginal cavity 12 such as, for example, adjacent the cervix 20; nearer the proximal end of cavity 12; and adjacent the vaginal orifice 16, as shown by dotted lines in FIG. 1A. Alternatively, the device may optionally be shorter than shown or longer than shown, for example, long enough to extend along the majority or along the entire length of the vaginal cavity, in which case it would extend from adjacent the cervix, or nearly adjacent the cervix, to the vaginal orifice, or nearly adjacent the vaginal orifice. The actual length of the deployed device may be selected depending on the user, as discussed further herein.

It may be noted that, in the embodiment shown in FIG. 1A, device 10 has a cup-shaped structure having a semi-ovate configuration, although other configurations such as, for example, a cone, a truncated cone, a polyhedron or a cylinder are also possible. Additionally, while the embodiments of the present invention may be described herein as being "cup-shaped," this should be understood as a structure having an open distal end and a closed proximal end, the structure having an interior volume.

Figure 1B:
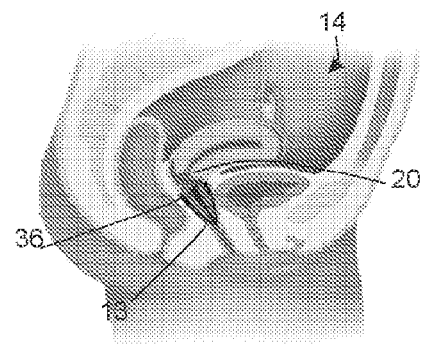
FIG. 1B is a side view of an intravaginal device according to additional embodiments of the present invention, shown in an exemplary position within a vaginal cavity.
Figure 1C:
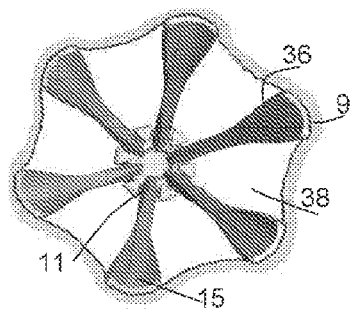
FIG. 1C is a cross-sectional view of the device shown in FIG. 1A, taken in the direction of lines C-C therein.
Figure 1D:
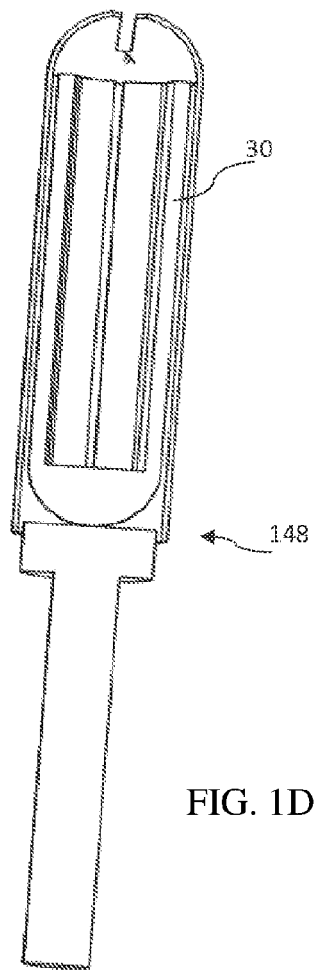
FIG. 1D is a side view of a device according to FIG. 2A, according to embodiments of the present invention, the device shown in a compressed/folded/deformed configuration inside an applicator, wherein the applicator is shown in cross-section, for clarity.

With additional reference to FIG. 1C, device 10 includes a plurality of axially extending elements 36 circumferentially spaced about the device and connected at their proximal ends 11, and a membrane 38 attached to the axially extending elements, as discussed herein. While in the embodiment shown in FIGS. 1A and 1C, device 10 includes six axially extending elements 36, it will be appreciated by persons skilled in the art that, if desired, a device may be provided with more or fewer axially extending elements, as discussed herein. Axially extending elements 36 apply a radially outward force to vaginal wall 9, as discussed further herein.

Optionally, each axially extending element may have a uniform width all along its length. Alternatively, at least one axially extending element may have a non-uniform width, for example, being thinner at its proximal end 11, relative to a thicker distal end 15; being narrower at its proximal end 11, relative to a wider distal end 15; being thicker at its proximal end 11, relative to a thinner distal end 15, or being wider at its proximal end 11, relative to a narrower distal end

15. Optionally, the circumferential extent of the distal end 15 of at least one axially extending element may be, for example, 2, 3, 4, or 5 times the circumferential extent of the proximal end 11 of the at least one axially extending element.

In embodiments, the device may have a volume of from approximately 10-50 ml, although smaller or larger volumes are also possible.

Referring now to FIG. 1B, there is shown an intravaginal device 13 according to some embodiments of the present invention, as discussed further herein. The device includes a plurality of axially extending elements 36 similar to those shown in FIG. 1C, but device 13 has no membrane attached to the axial elements. Device 13 may be positioned anywhere along vaginal cavity 12, as discussed above with regard to device 10. Alternatively, device 13 may optionally be shorter or longer, for example, long enough to extend along the majority or along the entire length of the vaginal cavity, in which case it would extend from adjacent the cervix, or nearly adjacent the cervix, to the vaginal orifice, or nearly adjacent the vaginal orifice. The actual length of the deployed device may be selected so that it best suits the user, as discussed further herein, or according to its intended use, as discussed herein.

Figure 2A:
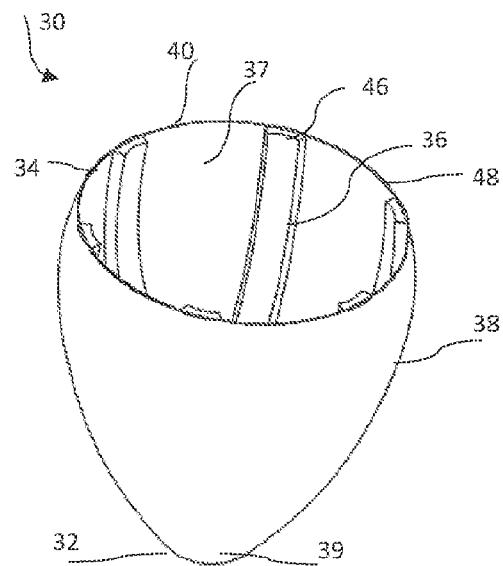
FIGS. 2A-B are perspective views of a device according to embodiments the present invention.

With reference to FIG. 2A, there is shown a perspective view of a device 30 according to a first embodiment of the present invention, the device having a proximal end 32 and a distal end 34, the device 30 shown in an open configuration.

Device 30 includes a plurality of axially extending elements 36. While in the embodiment shown in FIG. 2A, device 30 includes six axially extending elements 36, it will be appreciated by persons skilled in the art that, if desired, a device may be provided with more or fewer axially extending elements, depending on various factors such as, for example, dimensions of the axially extending elements and materials used. The device has a plurality of axially extending elements, which may optionally facilitate the forming of a seal between the device and a vaginal cavity, as discussed further herein. Optionally, the device has at least 5 axially extending elements.

In device 30, axially extending elements 36 are generally convex, at least along a portion of their length and, optionally, they may be configured such that their distal ends 46 are substantially parallel at the distal end 34 of device 30, as shown in FIG. 2A.

It will be appreciated by persons skilled in the art that axially extending elements 36 may optionally be formed as a single element, as discussed further herein. Alternatively, axially extending elements 36 may be formed as separate elements which may be connected at their proximal ends (not shown in FIG. 2A) by any means such as, for example, gluing, heat welding, ultrasonic welding, overmolding, dip molding, and fastening with a fastener or by a hinge.

Device 30 is additionally provided with a membrane 38 disposed outside the axially extending elements 36, the membrane having an edge 40 at device distal end 34. In embodiments, the membrane 38 may have a thickness in the range of from 10-1000 microns, and optionally may be manufactured by any suitable method such as, for example, an extrusion process, dipping, injection molding, double injection molding, overmolding, dip molding, CNC (computer numerical control) machining, vacuum forming, and 3-D printing.

According to some embodiments, the ribs and/or the membrane may be formed of, for example, Nylon12™, polypropylene, or from a biodegradable polymer PLA or of any suitable member of the polyolefin family such as, for example, polycarbonate or polyurethane, optionally having a Young's modulus in the range of from 0.1-50.0 MPa. Optionally, the axially extending elements may be fabricated from nitinol or stainless-steel wire. The membrane, for example, may optionally be fabricated of any or a combination of the following: a non-elastic material, an elastic material, a biocompatible material, a biodegradable material, and an antibacterial material. Optionally, the membrane includes nano-antimicrobial material such as, for example, silver particles or it can contain antibacterial pattern like Sharklet™

In embodiments, the relative elasticity of the membrane and the axially extending elements determines the configuration of the device, at least at the device distal end. According to some embodiments, the membrane is elastic and a ratio of elasticity of the membrane to elasticity of the axially extending elements is in the range of from 1:1 to 500:1, inclusive. Exemplary ratios may be, for example, 1:1, 5:1, 10:1, 50:1, 100:1, 200:1, 300:1, 400:1, and 500:1, as well as any intermediate ratios. Alternatively, the membrane may be non-elastic, and a ratio of elasticity of the membrane to elasticity of the axially extending elements may be 0 (zero).

In some embodiments, the membrane 38 may be attached to at least some of the axially extending elements 36, either at the top edges of the axially extending elements and/or along the length of the axially extending elements by any means such as, for example, gluing, heat welding, or ultrasonic welding. Alternatively the membrane 38 may be attached by pins or other protrusions extending out from the axially extending elements toward the membrane. It should be noted that any of the discussed means for attaching the membrane to at least some of the axially extending elements may be employed for any of the alternative embodiments of the invention discussed herein.

According to some embodiments, the axially extending elements cause the membrane to be stretched or stressed. In embodiments, due to this stretching/stressing of the membrane, the membrane is biased to contract when in a deployed condition, as discussed further herein. It should be noted that the device 30 has no rigid rim at the device distal end 34. However, in embodiments, elements 36 together with membrane 38 are configured to create a seal between the device 30 and a vaginal wall and to retain the device in its position and in its open configuration within the vaginal cavity, as discussed herein. In some embodiments, the axially extending elements 36 may be predisposed to extend radially outwardly, thereby exerting an outward radial force on an inner surface 37 of the membrane. The membrane, as well as any attachment means between the membrane and the axially extending elements, must be strong enough to withstand the outward radial force of the axially extending elements. The device distal end 34 is wide enough to exert a radially outward force on the vaginal wall of the vaginal cavity when the device is positioned in the vaginal cavity. The outward radial force is sufficient to create a seal between the device and the vaginal wall, at least at the distal end of the device. The force necessary to create the seal may be in the range of from 0.1-2 Kg (1-20 N), along the lip as discussed herein. The outward radial force is also sufficient to retain the device in its position within the vaginal cavity, once deployed therein.

As will be understood by persons skilled in the art, the outward radial force may also cause the potential vaginal cavity, which is normally collapsed, to remain open, as long as the device is deployed therein.

It is a further feature, in embodiments of the present invention that the outward radial force applied by the device to the vaginal wall is sufficient to stretch the vaginal wall, so that the device is maintained in position in the vaginal cavity. Due to the presence of the membrane, the outward radial force is also sufficient to seal the device against the vaginal wall.

It may be noted that the axially extending elements 36 are shown as extending to the distal end 34 of device 30, but not extending distally beyond the lip 48, thereby ensuring sealing engagement of the membrane with the vaginal wall. Optionally, the axially extending elements may be provided with edges that are rounded and/or widened and/or blunt, in order to prevent harm to tissue.

A particular feature of some embodiments is that there is no rigid rim at the distal end of the device to exert a radial force against the vaginal wall. In some embodiments, at least most of the outward radial force is provided by the elasticity of the axially extending elements.

It may be noted that, in the embodiment shown in FIG. 2A, when the device 30 is in a deployed configuration, the membrane 38 is stretched over the axially extending elements 36, due to their convexity and the relative dimensions of the elements 36 and the membrane 38. The membrane may limit the radially outward expansion of the axially extending elements. For example, the axially extending elements alone (without a membrane) may be predisposed to expand such that they may define a structure having a diameter at its distal end within a range of from 40-90 mm. Optionally this diameter is approximately 70 mm. However, when the membrane is stretched over the axially extending elements, as noted above, this limits expansion of the structure to a distal end diameter of, for example, from 25-60 mm. The exact deployed diameter of the device distal end will depend on a combination of the radially outward force of the axially extending elements and the maximum diameter of the membrane. Optionally, in embodiments where the membrane is elastic, the maximum diameter of the membrane is dependent on its elasticity. It is possible to provide a variety of sizes of the device, having different combinations of these parameters. The choice of size is selected for the individual user, as discussed herein.

It should also be noted that a vaginal passageway of a human female is essentially a collapsible tube having a diameter in the range of from 10-36 mm, depending on the individual, and that this diameter may change over time, due to a variety of factors including age, birth of a child, and general health. An intravaginal device in accordance with embodiments of the present invention, when deployed, will cause the vaginal wall to stretch, at least where it contacts the device distal end. For example, for a woman whose vaginal passageway has a diameter of 36 mm, an intravaginal device having a distal end diameter of 45 mm will cause the vaginal wall to stretch to a diameter of 45 mm, at least at the device distal end.

It is a particular feature that the device causes the vaginal wall to stretch at least at the device distal end thereof, for a number of reasons. First, the stretched vaginal wall is biased to move radially inwardly so that it conforms to the outer surface of the device, at least at its distal end. This aids in providing a seal between the device and the vaginal wall. Second, it should be noted that any device inserted into the vaginal cavity may move downward, due to gravity, unless held in place by some force such as, for example, friction. The intravaginal device may optionally be made of a low friction material such as, for example, silicon, and a force other than friction maintains the device in position so that it does not move downward in the vaginal canal. To that end, the bias of the stretched vaginal wall will prevent the device from moving downward in the vaginal canal.

In some embodiments, prior to deployment, e.g., when contained within an applicator, for example, as discussed herein, the device may have a diameter of approximately 8-20 mm. When deployed, in embodiments, the axially extending elements expand radially outwardly while the membrane is stretched over the axially extending elements, thereby limiting their outward expansion. The device distal end is wide enough to stretch the vaginal wall and to create a seal between the device and the vaginal wall, in some embodiments, as noted herein.

In some embodiments the membrane is configured as a cup-shaped component, as shown in FIG. 2A. However, in embodiments, a membrane may be formed with an opening at a proximal end 39 thereof, the proximal end of the membrane sealed by any suitable method such as, for example, heating, tying, sealing with a sealing mechanism, and fastening with a fastener.

In embodiments, the membrane 38 is specifically configured and optionally, the axially extending elements may be elastically predisposed to expand radially outwardly against the membrane, such that they together form the cup-shaped structure shown, having a lip 48 beginning at edge 40 of membrane 38 and extending proximally for a distance D (FIG. 1A) in the range of from 1 mm to 2 cm. It should be noted that, in embodiments, the width of lip 48 may be determined by at least one of the shape of the axially extending elements, and the relative forces applied by the axially extending elements (radially outward) and optionally the membrane (optionally radially inward). For example, for a device having a cylindrical shape, a lip may be defined along the entire length of the device.

Optionally, the axially extending elements 36 (FIG. 2A) also prevent radial collapse of the membrane, such that the device maintains its cup-shaped configuration when in position within the vaginal cavity.

Optionally, axially extending elements 36, 36b (FIGS. 2B-C), 36d (FIG. 2D) are provided with a textured surface or protrusions (not shown) configured to retain the membrane in position relative to the axially extending elements. Optionally, the membrane 38 is attached to the axially extending elements, at any portion therealong, by any suitable method such as, for example, gluing or welding.

Optionally, the membrane may have an outer surface configured to increase friction between the device and an inner surface of the vaginal cavity. This feature may facilitate sealing between the membrane and the vaginal wall.

Optionally the membrane has embedded therein or has thereon at least one medication to treat the user while using the device. Suitable medications that may be used with embodiments of the invention include, for example, L-Lactide and citric acid to control vaginal pH, and azole antifungal agents to treat yeast infection.

Optionally, the membrane and the axially extending elements are fabricated such that the membrane longitudinal axis is substantially parallel to the axis of the vaginal passageway in the vaginal cavity.

It will be appreciated by persons skilled in the art that any of the above-described features may optionally apply to any of the embodiments described herein.

Figure 2B:
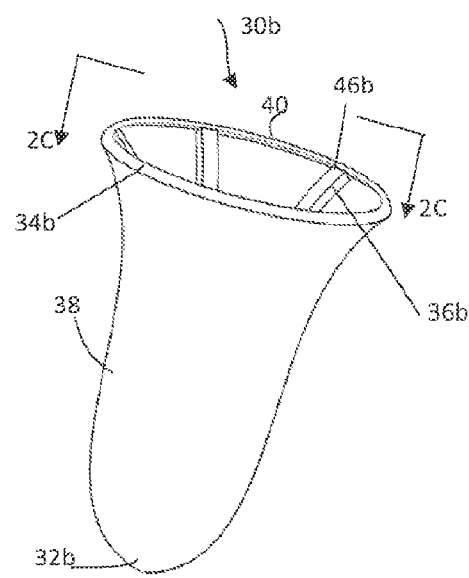
Figure 2C:
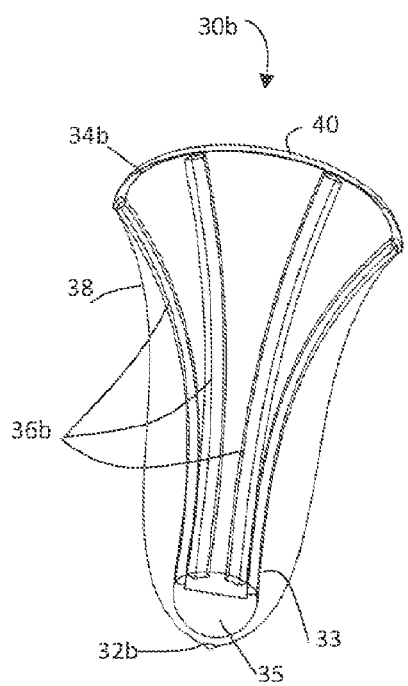
FIG. 2C is a cross-sectional view of the device shown in FIG. 2B, taken in the direction of arrows C-C therein.

With additional reference to FIGS. 2B-C, there is shown an alternative embodiment of a device 30b having a plurality of axially extending elements 36b and a membrane 38. Device 30b is similar in function to device 30 (FIG. 2A), except that axially extending elements 36b are concave at least along a portion of their length. Optionally, axially extending elements 36b may be configured such that their proximal ends 33 are substantially parallel. Optionally, proximal ends 33 of axially extending elements 36b may be connected by means of a fastening element 35 which, in some embodiments, forms a base of the axially extending elements.

The outer configuration of the device depends on both the membrane and the axially extending elements. For example, a structure having at least a partially concave configuration may be formed by axially extending elements which are concave along at least a portion of their length such as, for example, as shown in FIGS. 2B-C. Alternatively, an embodiment having axially extending elements that have a proximal concave portion and a distal convex portion such as, for example, shown in FIG. 2D, or vice-versa, may have at least a partially concave configuration. Other possibilities for having an outer shape with at least a partially concave configuration include a device wherein the outer membrane is narrower at at least one portion.

It may be noted that, due to the concavity of the axially extending elements, in some embodiments, the membrane may not be held taut/stretched along the entire length of the device, and may remain loosely disposed about a portion of the axially extending elements such as, for example, near a proximal end 32b of the device. However, it will be appreciated by persons skilled in the art that, at least at a distal end 34b of device 30b, when in the deployed configuration, the membrane 38 is held taut/stretched by the distal ends 46b of the axially extending elements 36b.

Figure 2D:
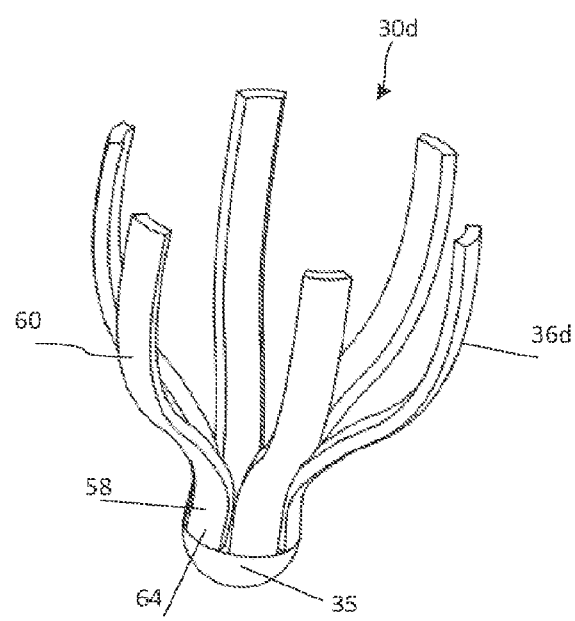
FIG. 2D is a perspective view of a device according to an alternative embodiment of the present invention, a portion having been removed for clarity.

With additional reference to FIG. 2D, there is shown a device 30d according to an alternative embodiment of the present invention, the membrane portion having been removed for clarity. Device 30d includes axially extending elements 36d which are similar in function to axially extending elements 36 (FIG. 2A). However, it may be noted that each of the axially extending elements 36d has a partly concave portion 58, adjacent a proximal end 64 of element 36d, which curves toward the outside of the device, and a partly convex portion 60, distal to portion 58, which curves toward the inside of the device. This particular structure of elements 36d results in proximal ends 64 of elements 30d being disposed adjacent to each other, in a substantially parallel configuration, adjacent a fastening element 35.

A particular feature of device 30d is that, due to the structure of the proximal ends 64 of axially extending elements 36d, the device may be more easily grasped at its proximal end 52 for removal, as discussed further herein. Alternatively, if desired, the device may be provided with a removal element (not shown), as discussed herein, for removal of the device from the vaginal cavity.

The particular configuration of the axially extending elements, whether convex, concave, linear, or any combination thereof, may have at least one particular advantage. For example, according to some embodiments, a convex configuration may be more comfortable when being inserted. According to some embodiments, a concave configuration may have the potential advantage of providing better anchoring against the vaginal wall. In embodiments, a device having linear axially extending elements may be easier to insert into an applicator and/or may be more easily deployed.

It should be noted that any of the embodiments discussed herein may optionally be provided with an absorbent material having any combination of the features noted above.

Device 30, for example, has been described above as having a generally cup-shaped configuration suitable for being retained within a vaginal cavity. It should be noted that, when in the vaginal cavity, device 30 is in the expanded cup-shaped configuration shown in FIG. 2A, wherein the lip 48 has a first diameter, at the device distal end 34, defined by the axially extending elements 36.

In some embodiments, in order to facilitate insertion of device 30 into the vaginal cavity, device 30 is radially compressible to a second cup-shaped configuration, wherein the axially extending elements 36 define a second diameter smaller than the first diameter. Alternatively, device 30 may be foldable or otherwise deformable to a second configuration, in order to facilitate its insertion into the vaginal cavity. In the radially compressed/folded/deformed configuration, membrane 38 may fold inward, between the axially extending elements 36, or fold outward.

When in the second configuration, device 30 may optionally be inserted into and retained within an applicator 148 (FIG. 3) to facilitate insertion of the device 30 into the vaginal cavity and deploying of device 30 to a suitable position within the vaginal cavity. A suitable applicator may be, for example, of a type known in the art which includes a container portion and a plunger portion, which need not be discussed further herein. Alternatively, any other suitable applicator may be provided for deploying a device in accordance with any of the herein-discussed embodiments to a suitable position within the vaginal cavity. Use of an applicator is discussed further below, with reference to additional embodiments and with reference to FIG. 4.

It should be noted that any of the devices discussed herein may optionally be radially compressible and/or foldable and/or otherwise deformable, and insertable into a suitable applicator having an inner diameter in the range of from 8-20 mm, in order to facilitate insertion of the device into the vaginal cavity, in a manner similar to that discussed above with regard to device 30.

Device 30 may optionally be removed manually from the vaginal cavity, by grasping the proximal end of device 30 and pulling the device through the vaginal orifice 16 (FIG. 1A). Optionally, device 30 may be provided with a removal element, at a proximal end of the device, the removal element configured to facilitate removal of device 30 from the vaginal cavity. An exemplary removal element is, for example, the string 1616 shown in the embodiment of FIG. 6B.

Optionally, in some embodiments, pulling of the removal element may actuate/facilitate collapsing of the device, whereby the axially extending elements are moved inwardly to allow removal of the device from the vaginal cavity.

A variety of valves may optionally be provided to any of the devices in accordance with embodiments of the present invention discussed herein such as, for example, at a distal end of the device. Any such valve may optionally provide an additional feature to a device according to embodiments discussed herein, whereby any material that has entered into the interior of the device will be retained therein. These valves are of types known in the art such as, for example, a duckbill valve, a shutter-type valve, and other one-way valves.

In embodiments, the valves are one-way valves that allow entry of menses discharge, for example, into the interior of a device. Once menses charges has been collected inside the device, the collected menses discharge cannot exit the device due to the presence of the valve, regardless of the orientation of the device (i.e., if the user is lying down).

Figure 3A:
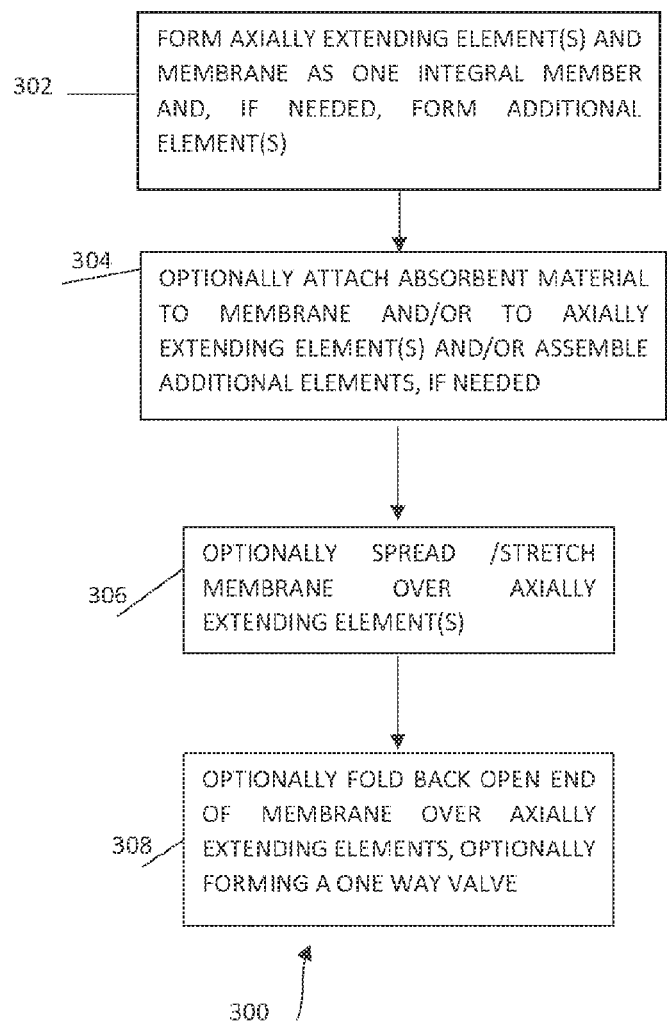
FIGS. 3A-B are flow charts illustrating methods of manufacturing a device according to embodiments of the present invention.

With reference to FIG. 3A is shown a flow chart illustrating a method 300 of manufacturing a device according to embodiments of the present invention, as discussed herein.

At 302, a device having both a plurality of axially extending elements and a membrane is formed as one integral member and, if needed, additional elements are formed. Optionally, at 304, absorbent material is attached to the membrane and/or to the axially extending elements, and/or additional elements are assembled, if needed. At 306, if necessary, the membrane is spread and/or stretched over the axially extending elements. Optionally, at 308, the open end of the membrane is folded back over the axially extending elements, optionally forming a one-way valve within the device.

Figure 3B:
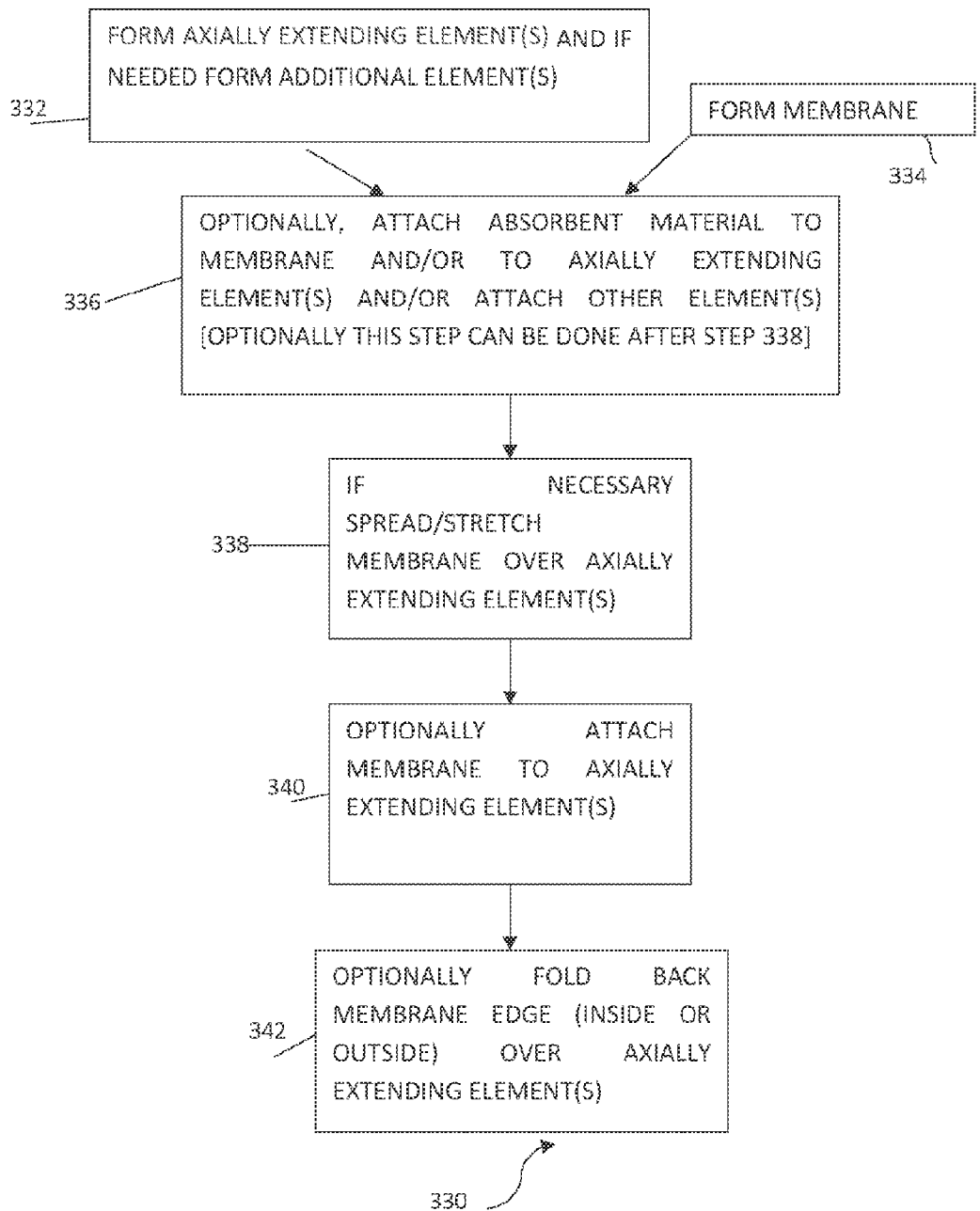

Referring now to FIG. 3B, there is shown a flow chart illustrating an alternative method 330 of manufacturing a device according to embodiments of the present invention, as discussed herein. At 332, optionally, a plurality of axially extending elements is formed into a structure for defining, for example, a cup-shape, cone-shape, truncated-cone shape, polyhedron-shape, or cylinder shape. Optionally, if the structure defined by the axially extending elements is not closed at both ends, the structure may be closed at a proximal end thereof by, for example, a fastener, as discussed herein Also, if needed, additional elements may be formed at this stage. At 334, a membrane is formed. At 336, absorbent material is optionally attached to the membrane and/or to the axially extending elements. Also, other elements may be attached, if needed. Optionally, step 336 may be performed after step 338. At 338, if necessary, the membrane is spread and/or stretched over the axially extending elements. Optionally, at 340, the membrane may be attached to the axially extending elements. Optionally, at 342, the open end of the membrane is folded back over the ribs, optionally forming a one-way valve within the device.

While the method of each of FIGS. 3A-B has been described with regard to a plurality of "axially extending elements," it should be understood that any suitable element (s) which may expand radially outwardly, as discussed herein, or any suitable supporting structure may be utilized in accordance with embodiments of the present invention.

Figure 4:
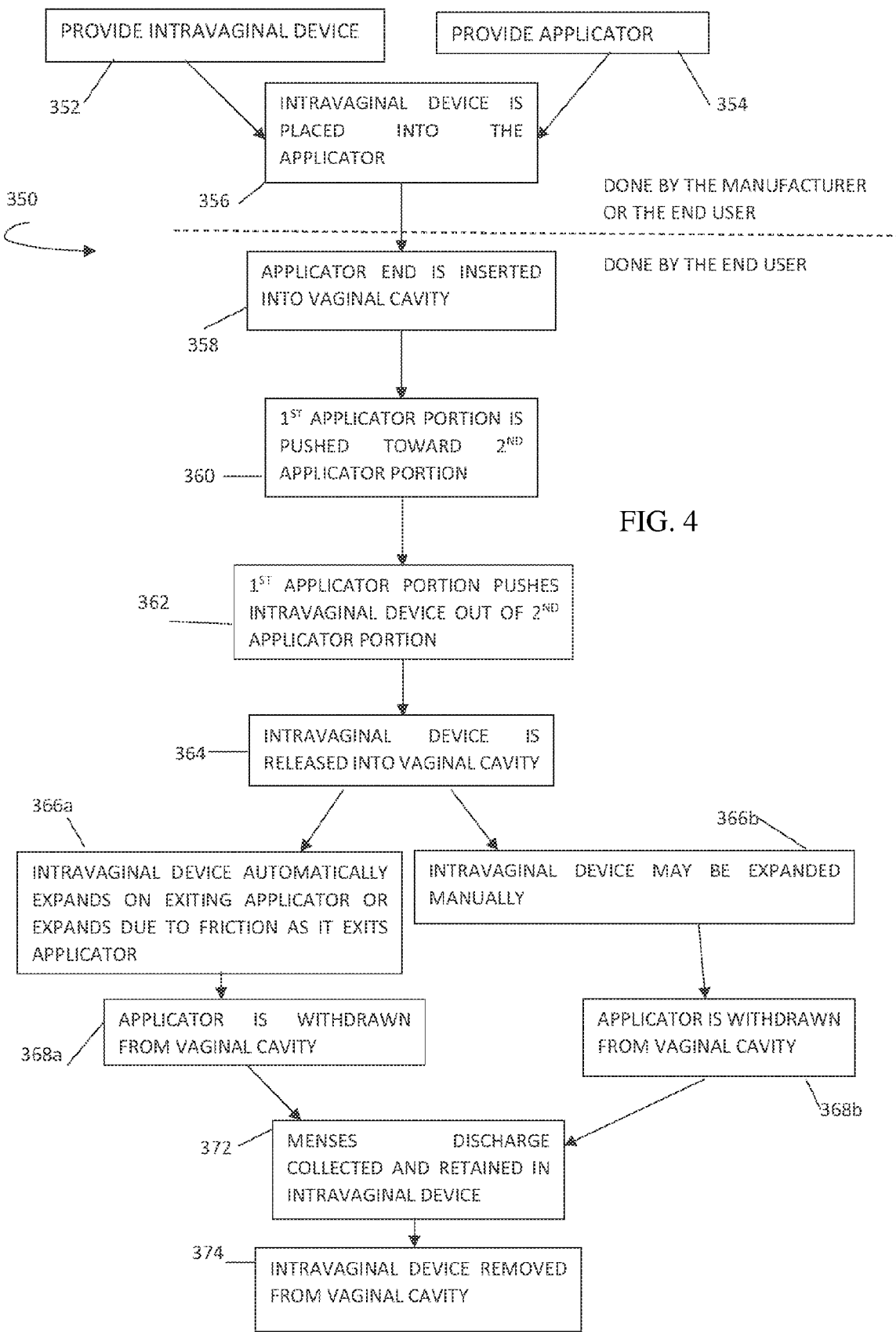
FIG. 4 is a flow chart illustrating a method of use of a device according to some embodiments of the present invention.

With reference to FIG. 4, there is shown a flow chart illustrating a method 350, in accordance with embodiments of the present invention, the method for utilizing any of the intravaginal devices discussed herein. At 352 there is provided an intravaginal device such as, for example, any of the intravaginal devices discussed herein with reference to any of the embodiments of the invention discussed herein and, at 354, a suitable applicator is provided for the intravaginal device provided in step 352. At 356, the device is collapsed/folded/deformed and/or radially compressed as discussed herein, and is placed into the applicator. It should be noted that collapsing/folding/deforming/radial compression of the device and its insertion into an applicator may be performed, for example, at a location of manufacture of the device, and need not be performed by a user of the device. When collapsed and/or radially compressed, the membrane may optionally fold inward toward the interior of the device. Alternatively, the membrane may fold outward and be foldable against other components of the device. All steps up to this point (above dotted line) may optionally be performed by a manufacturer of the device.

From this point onward (below dotted line), all steps may optionally be performed by a user of the device. At 358, the applicator distal end is inserted into the vaginal cavity, as discussed herein. At 360, the applicator is activated by pushing a first portion (e.g., plunger 156) into a second portion (e.g., container portion 154) housing the intravaginal device, the applicator first and second portions being shown, for example, in FIG. 10A.

At 362, the first applicator portion pushes the intravaginal device out of the second applicator portion, after which the intravaginal device is released into the vaginal cavity, as shown at 364.

At 366a, according to some embodiments discussed herein, the device may be predisposed to automatically expand radially outwardly or may be caused to expand radially outwardly upon exiting the applicator container portion, such that the device creates a seal against the vaginal wall when it is ejected from the applicator, as discussed herein.

At 366b, according to some embodiments, the device does not automatically expand radially outwardly, and so the device may be manually actuated to expand radially outwardly simultaneously with or immediately after its ejection from the applicator, so as to achieve a seal against the vaginal wall. Such actuation to expand radially outwardly may be initiated, for example, pulling on an actuator element/removal element, as discussed herein.

The applicator may, optionally, then be withdrawn from the vaginal cavity, at 368a/368b. At 372, the device may collect menses discharge or, alternatively, may perform any other function for which the device is intended, as discussed herein. At 374, the device may be removed from the vaginal cavity, as discussed herein.

With reference to FIGS. 5A-C there is shown a device 500 in accordance with an alternative embodiment of the invention. Device 500 includes a membrane 508 extending from a proximal end 504 to a distal end 506 of device 500. Membrane 508 may be similar in structure and function to the membrane discussed with regard to FIG. 2A, and may optionally be fabricated, for example, from an elastic or non-elastic material. Membrane 508 is optionally provided with a radially-inwardly extending valve 548, as discussed herein. Valve 548 extends from a membrane distal portion 568 downwardly into the interior of device 500. Valve 548 ensures retention of collected material inside device 500, for example, when the user is lying down or when the device is being/has been removed. Valve 548 may be any kind of one-way valve.

Device 500 is also provided with a plurality of ribs 502, shown most clearly in FIG. 5B, wherein the membrane and optional valve components of the device have been omitted, for clarity. Ribs 502 extend from a proximal end 504 to a distal end 506 of device 500. In the embodiment shown, three ribs 502 are visible (in the cross-section). However, it should be understood that device 500 may optionally be provided with any suitable number of ribs such as, for example, 4, 5, 6, 7, or 8 ribs. Each rib 502 includes an elongate axial portion 514 having a distal end 514a and a proximal end 514b, wherein the rib proximal ends are hingedly connected, at device proximal end 504, for example, by a hinge element 510. Hinge element 510 may optionally be any suitable element which provides a hinged connection between rib proximal ends 514b while allowing pivoting of rib proximal ends 514b and thereby movement of ribs 502, whereby rib distal ends 514a are movable radially inwardly from a first configuration shown in FIG. 5B to a second configuration, wherein the ribs 502 are substantially parallel and define a cylindrical space having a diameter D (FIG. 5D). Similarly, when in the second configuration, rib distal ends 514a are movable radially outwardly to the first configuration (FIG. 5B).

Device 500 is also provided with an actuator element 512 having an attached pullable element such as, for example, a string 540 attached to actuator element 512, the string extending through an opening 546 at device proximal end

504. Actuator element 512 may optionally be fabricated from a flexible elastomer such as, for example, silicon, having a shore hardness in the range of from 30 shore A to 70 shore A. Alternatively, actuator element 512 may be fabricated from a non-elastic material having a shore hardness of up to 80 shore D. The actuator element 512 may optionally be formed by injection molding and the string 540 may be formed of cotton material, for example, as known in the art. Optionally, a portion of the string may be overmolded with the actuator element.

Actuator element 512 and string 540 facilitate conversion of device 500 from the second configuration (FIG. 5D) to the first configuration (FIG. 5B), as discussed in detail below.

With additional reference to FIG. 5D, device 500 is shown in position within a suitable applicator 530, the membrane 508 and optional valve 548 of device 500 having been omitted and a portion of the components and applicator having been enlarged for clarity. Applicator 530 includes a container portion 532 and a plunger portion 534, for example, as known in the art, and includes optional slits/score lines 536, at applicator distal end 537, for facilitating ejection of the device from the applicator.

In the embodiment shown, actuator element 512 includes an outer surface 528 including a distal tapering portion 520 and a proximal radial portion 522. Tapering portion 520 terminates in a flange 524 extending distally and outwardly at actuator element distal end 518. Radial portion 522 terminates at a base 526 at actuator proximal end 516, flange 524 being wider than base 526, as seen most clearly in FIG. 5D. It should be noted that flange 524 has an outer diameter larger than D and that radial portion 522 has an outer diameter smaller than D.

In order to insert device 500 into applicator 530, ribs 502 should be moved to the configuration shown in FIG. 5D. This is achieved by moving rib distal ends 514a radially inwardly, such that rib proximal ends 514b pivot on hinge element 510 until ribs 502 are approximately parallel, as shown in FIG. 5D. Actuator element 512 is then positioned relative to ribs 502 such that radial portion 522 of actuator 512 is disposed between rib distal ends 514a. Since the outer diameter of flange 524 is wider than D, the actuator may optionally rest on the rib distal ends 514a and is prevented from moving proximally along the ribs 514, as long as the ribs remain parallel.

It should be noted that ribs 502, when housed inside applicator 530, do not apply any outward pressure to inner walls 533 of the applicator. There are, in fact, no forces applied on the rib structure until actuator element 512 is actuated, as discussed herein. There is no creep or plastic deformation of the material when device 500 is disposed within applicator 530.

It should also be noted that membrane 508 (not shown in FIG. 5D) is flexible/foldable such that, when the device is inserted into applicator 530, the membrane 508 is in a compressed/folded configuration.

Device 500 may optionally be ejected from the applicator 530 by pushing the applicator plunger 534 into the applicator container portion 532, for example, as known in the art. This action moves device 500 distally, until it comes into contact with the applicator distal end 537. Continued pushing of the applicator plunger forces device 500 against applicator distal end 537, which causes slit/score lines 536 to open/rupture, thereby allowing device 500 to be ejected from the applicator 530. Once device 500 has been ejected from applicator 530, while the applicator container portion 532 is held in position with one hand the actuator element 512 may optionally be moved from the position shown in FIG. 5D to the position shown in FIGS. 5B-C by pulling string 540 (with the other hand) in the direction of arrow 538. Optionally, the string need not be pulled manually, as it may be pulled by a portion of the applicator, during insertion of the device. As string 540 is pulled, actuator element 512 is advanced along a path 542 from device distal end 506 to device proximal end 504, while being supported by rib axial portions 514. At the same time, as actuator element 512 advances proximally, tapering portion 520 of the axial element 512 applies pressure to rib axial portions 514, causing rib proximal ends 514b to pivot on hinge element 510, thereby moving rib distal ends 514a radially outwardly, to the configuration shown in FIGS. 5B-C.

Base 526 of actuator element 512 is provided with a radial flange 544 that extends outwardly from base 526 and has a diameter smaller than that of radial portion 522 but slightly larger than that of opening 546. When actuator element 512 has been advanced proximally such that it reaches device proximal end 504, it is prevented from moving further by flange 544 which abuts device proximal end 504. At least one of flange 544 and a portion of device proximal end 504 is provided with a flexible/deformable portion such that application of an additional force of at least F1 on string 540 in the direction of arrow 538 will force flange 544 on base 526 through opening 546, thereby locking ribs 502 in position, but further movement of actuator element 512 will be prevented by radial portion 522 of actuator which abuts against device proximal end 504.

Once flange 544 has been forced through opening 546, actuator element 512 has traveled to its most proximal position, as shown in FIGS. 5B-C and, consequently, ribs 502 are in the configuration shown, whereat the device 500 causes the vaginal wall to stretch at least at the device distal end thereof. This provides of a seal between the device and the vaginal wall, and facilitates retaining of the device in position in the vaginal cavity, as discussed herein.

It may be noted that, in the embodiment shown in FIG. 5C, membrane 508 may optionally fit loosely around a portion of ribs 502, at least at the device proximal end 504. However, the membrane 508 must fit snugly around the ribs at least at the device distal end 506 when deployed within the vaginal cavity, so as to ensure a seal between the device and the vaginal wall. Alternatively, if desired, membrane 508 may be replaced with a membrane which is narrower such that, when the membrane is stretched, by outward radial movement of rib distal ends 514a, it fits snuggly about the ribs. Such an embodiment may appear similar to that of FIG. 2A, at least when viewed from the side.

When it is desired to remove device 500 from the vaginal canal, further pulling on the string 540 will cause the device to be pulled proximally along the vaginal canal until it exits the vaginal canal via the vaginal orifice 16 (FIG. 1A).

If desired, device 500 may be provided with superabsorbent material, for example, as known in the art and discussed herein.

Reference is now made to FIGS. 6A-6C, which illustrate an intravaginal device 1600, in accordance with a non-limiting embodiment of the invention.

Device 1600, as seen in FIG. 6B, may include arms 1602 that pivot from a proximal base 1603, such as but not limited to, by a living hinge or other pivot. The illustrated embodiment shows six arms 1602, but the invention may be carried out with any number of arms. The arms 1602 may be deployed outwards by struts 1604 that are coupled to arms 1602 and to a central shaft 1606 which slides in a central tube 1608. Each strut 1604 may include a first end 1610 pivotally coupled to a distal end of shaft 1606, and a second end 1612 pivotally coupled to arm 1602. Each strut 1604 may be constructed as a pair of members 1604A and 1604B, which may be slightly bowed or curved. The double-member construction of the arm provides increased rigidity.

A string 1616 is coupled to shaft 1606. Initially the device 1600 is inside an applicator or sheath 1620, shown in broken lines in FIG. 6A. In this orientation, the struts 1604 are folded inwards such that the second ends 1612 point towards the proximal end of the device (base 1603). The distal end of shaft 1606 is spaced distally from the distal end of tube 1608. The applicator 1620, with device 1600 inside it, may be inserted in the vagina. The device 1600 may then be pushed out of the applicator 1620. Upon movement out of the applicator 1620, the struts 1604 move radially outwards to the position shown in FIG. 6B. Shaft 1606 may be locked at this position, such as by a portion of shaft 1606 clicking into a detente in tube 1608 or other mechanism.

In this deployed position, the arms 1602 are tautly held by the expanded struts 1604. The arms 1602 are surrounded by a covering 1622 and the distal end of the covering 1622 may be closed by a one-way valve 1624. The device 1600 is now securely held in the vagina to capture therein menstrual blood or other fluids. The one-way valve 1624 seals the fluid in the device.

When it is desired to remove device 1600, the string 1616 may be pulled proximally in the direction of arrow 1617 (FIG. 6B), which moves shaft 1606 proximally until the distal end of shaft 1606 abuts against the distal end of tube 1608. to bring the shaft 1606 out of locked engagement with tube 1608 so that shaft 1606 now protrudes proximally out of tube 1608, as seen in FIG. 6C. In this orientation, arms 1602 start to fold inwards such that the second ends 1612 point towards the distal end of the device. The device 1600 can now be removed from the vagina.

With reference to FIG. 7 there is shown a device 1000 according to an alternative embodiment of the present invention. Device 1000 includes components similar in structure to those of device 30*d* (FIG. 2D) or that of FIGS. 6A-6C. Device 1000 may be deployed in and removed from a vaginal passageway in a manner similar to that of device 30*d*, and so these features need not be discussed again herein. It should also be noted that device 1000, in embodiments, need not be sealed against the vaginal wall, in some scenarios.

Device 1000 differs from device 30*d* in that device 1000 does not include a membrane, but is provided with a payload component 1010 on a most proximal portion 1020 of an interior 1030 of the device 1000. In embodiments, device 1000 is configured such that the payload component 1010 may be exposed to vaginal walls and/or fluids present in the vaginal canal.

Payload component 1010 may be, for example, of the type described in WO 2017/010080, but the size, shape, and location of the component may be modified from that shown, optionally, so as not to interfere with deployment, function, and/or removal of the device. Alternatively, the payload may be of any other type which may be exposed to the vaginal wall and/or to vaginal fluids and does not interfere with delivery of the device into the vaginal cavity and its deployment therein.

Provision of a payload component allows device 1000 to have a particular function or combination of functions that may optionally be performed when the device is positioned inside the vaginal passageway. These functions include, for example, the release of a substance into a vaginal cavity of the human female, monitoring pH level of the human female, monitoring body temperature of the human female, measurement of fetal heart rate, and monitoring of fetal body movements.

The following links/references show various examples of known devices that may be used for the above-discussed functions:
  a. Measuring pH: pH sensors available from Mettler Toledo Ltd., Israel
  b. Sensor for the simultaneous measurement of pH, temperature, and pressure:
  "A wireless micro-sensor for simultaneous measurement of pH, temperature, and pressure", Mahaveer K Jain, Qingyun Cai and Craig A Grimes, Smart Mater. Struct. 10 (2001) 347-353
  c. Sensors for measuring pH:
  "Review on State-of-the-art in Polymer Based pH Sensors," Olga Korostynska 1 , Khalil Arshak, Edric Gill and Arousian Arshak, Sensors 2007, 7, 3027-3042
  d. Measuring temperature:
  https://www.omega.com/pptst/55000.html or http://www.ti.com/lit/ds/symlink/lmt88.pdf
  e. Slow release of medication:
  https://en.wikipedia.org/wiki/Modified-release_dosage
  f. measuring amount of collected material
  https://www.cnet.com/news/smart-bluetooth-menstrual-cup-tracks-your-period/

In the embodiment shown, payload component 1010 is shown on the most proximal portion 1020 of device interior 1030, which is attached adjacent proximal ends 64 of the axially extending elements 36*d*. Also, payload component 1010 is shown as being cylindrical and having a length of about one third the length of device 1000. Optionally, payload component 1010 may be attached to an alternative location on device 1010, and/or may have an alternative shape and/or size, depending on its intended function, in such a manner that it does not interfere with collapsing of the device 1000 such as, for example, for insertion into a suitable applicator, or deployment of the device within the vaginal cavity. It should be noted that payload component 1010 may optionally be added to any one of the other concepts presented in this application and, optionally, according to some embodiments, the membrane may optionally be removed, if desired.

What is claimed is:

1. An intravaginal device comprising:
  arms, each of the arms has a proximal portion that pivots from a proximal base;
  struts, each of the struts has a first end coupled to a shaft arranged to slide in a tube and a second end coupled to one of said arms; and
  a string coupled to said shaft and arranged for pulling in a proximal direction, said arms having a stowed orientation in which said struts are folded inwards such that the second ends point towards a proximal end of said intravaginal device, and said arms having a deployed orientation in which said struts point radially outwards and tautly hold said arms in an expanded position in which distal ends of said arms define a distal open end, and wherein a covering surrounds said arms, and in the expanded position, a fluid can flow into said distal open end and the fluid is retained in said covering until the fluid is removed from said covering, and wherein each of said second ends is coupled to one of said arms in both the stowed orientation and the deployed orientation.

2. The intravaginal device according to claim 1, further comprising a one-way valve for closing said covering.

3. The intravaginal device according to claim 1, wherein in the deployed orientation, said shaft is locked relative to said tube.

4. The intravaginal device according to claim 1, wherein for each of said struts said first end is pivotally coupled to a distal end of said shaft, and said second end is pivotally coupled to the one of said arms.

5. The intravaginal device according to claim 1, wherein each of said struts comprises a pair of members.

6. The intravaginal device according to claim 5, wherein said pair of members are curved.

7. The intravaginal device according to claim 1, wherein said arms have a removable orientation in which said shaft protrudes proximally out of said tube and said second ends point towards a distal end of the intravaginal device.

8. The intravaginal device according to claim 1, further comprising a payload component coupled to a portion of said intravaginal device, said payload component comprising a substance delivery element or at least one sensor for sensing a biological feature.

* * * * *